| United States Patent [19] | [11] Patent Number: 4,715,813 |
| Mühlbauer | [45] Date of Patent: Dec. 29, 1987 |

[54] METHOD OF DETERMINING MATERIALS OF SUITABLE COLOURS FOR A TOOTH REPAIR LAYER OF PROSTHESIS FACET, AND A SAMPLE SET FOR APPLYING THIS METHOD

[76] Inventor: Ernst Mühlbauer, Fangdieckstrasse 61, 2000 Hamburg 53, Fed. Rep. of Germany

[21] Appl. No.: 880,733

[22] Filed: Jul. 1, 1986

[30] Foreign Application Priority Data

Jul. 4, 1985 [DE] Fed. Rep. of Germany ....... 3523982

[51] Int. Cl.$^4$ ............................................. A01C 19/00
[52] U.S. Cl. ..................................................... 433/26
[58] Field of Search ...................... 433/26; 634/99, 100

[56] References Cited

U.S. PATENT DOCUMENTS 1,582,122  4/1926  Clapp .................................. 433/25

*Primary Examiner*—Robert Peshock
*Attorney, Agent, or Firm*—Chilton, Alix & Van Kirk

[57] ABSTRACT

Method of determining materials of suitable colours for the base and top layers of a tooth repair layer or prosthesis facet with the aid of colour samples composed of a plurality of layers. Separate samples are used for the base and top layers. They are optically connected by wetting with a liquid. The liquid may also itself be used to form one of the sample layers.

10 Claims, No Drawings

METHOD OF DETERMINING MATERIALS OF SUITABLE COLOURS FOR A TOOTH REPAIR LAYER OF PROSTHESIS FACET, AND A SAMPLE SET FOR APPLYING THIS METHOD

DESCRIPTION

The invention relates to a method of determining materials of suitable colours for the base and top layers of a tooth repair layer or prosthesis facet with the aid of samples composed of a plurality of layers. The invention also relates to a set of samples suitable for applying this method.

Natural human teeth consist of variously coloured layers of varying transparency. For dental repairs and in the production of dental prostheses it is generally considered sufficient for the colour of the repair or top layer to be selected to approximate substantially that of the natural tooth by making use of colour samples.

The colour samples available in practice for this purpose are tooth- or wedge-shaped pieces of the material available for the top layer, or of an optically similar material. Since however for the purposes of this selection it is not only the colour of the top layer that is of importance, but also the colour of the optically participating deeper layers, the use of these samples frequently leads to errors in the selection of the colour. Samples of multilayer construction have therefore also already been proposed (DE-OS No. 26 41 740; DE-OS No. 14 91 198). Nevertheless, these samples were not successful in practice because the combination of a plurality of base and top layer colours in samples, in which these layers are joined fast to one another, leads to a multiplicity of individual samples which in practice cannot be successfully managed. The use of individual samples which can be loosely assembled does not often lead to useful results, because they are not optically joined together in the same manner as in the final assembled repair layer. If a very accurate colour selection is desired the dentist must therefore at the present time usually prepare a number of realistic trial samples of those repair materials which at first sight appear to him to be worthy of closer consideration. This is very complicated.

The problem underlying the invention is therefore that of providing a method and a set of colour samples suitable for that method, which will make it possible to determine suitable materials for the base and top layers of a tooth repair layer without the production of realistic trial samples and without requiring innumerable sets of colour samples.

The solution according to the invention consists in assembling separate samples of the base layer and top layer with optical connection by means of a layer of liquid.

The invention is based on the realization that the same optical connection as is present in the final result between the base and top layers, which are assembled directly and without the inclusion of a foreign air layer, is also obtained if a liquid wets the samples, because the refractive index of a liquid is substantially closer to that of the solids used than is that of air. The invention seeks to make the widest use of this realization in the field of production of samples for approximating dental repair material or dental prosthesis material to the natural colours of the patient's teeth.

In a first embodiment of the invention separate base and top layer samples are provided, but only one of each of them for each colour selected. The total number of samples is therefore comparatively small and easy to manage. For the purpose of forming a colour sample, they are assembled and optically connected together by enclosing a thin, transparent layer of liquid between them, this liquid layer wetting the two mutually facing surfaces of the samples. In this way an impression of colour optimally approximating the optical impression of the repair layer which it is intended to produce can be obtained.

The liquid selected for the optical connection between the samples will expediently be one whose refractive index comes as close as possible to that of the materials to be used, and which after use can easily be removed. Clear liquids, such as water, glycerine and oils, can advantageously be used.

As is known per se, it is possible in this context to make use of samples whose layer thickness varies, for example because of their conical shape. While the top layer samples are translucent, the base layer samples will usually be made opaque.

The invention is also suitable for imitating a three-layer combination, in which the layer to be placed between the top layer and the base layer is imitated by the liquid layer in the model. This is particularly convenient when the intermediate layer is used for colouring purposes, for example by means of known tints. In the case of photohardening tints, these can be used directly as the optical connection liquid between the samples of the base and top layers, since they do not harden during the use of the sample and therefore can easily be wiped off the samples. Instead, non-hardening sample tints can be used which optically resemble the tints subsequently to be used in the preparation of the repair layer and which can be removed from the samples more easily than the first-mentioned tints.

A set of colour samples for applying the method of the invention comprises separate, freely assemblable samples for the base and top layers and also optionally apparatus for introducing the optical connection liquid. The liquid itself may also be added to the set of colour samples in suitable containers. This may also include tints or sample liquids corresponding to tints.

If the liquid layer is coloured in order to imitate the action of tints, it is already used as an independent sample layer between the solid samples of the base and top layers. This principle can be further developed by using the layer of liquid as a sample of the top or base layer. Its use as a sample of the base layer is in particular very advantageous, because it is necessary to provide only solid samples of the available top layer and some sample liquids to imitate the base layer, these liquids being as opaque as is to be expected of the base layers, while they may also be coloured to correspond to the base layer colours used. Handling is very simple, because it is merely necessary to wet the rear of the top layer samples with the base layer sample liquids in question.

Conversely, the top layer materials concerned may be imitated by a sample liquid used in conjunction with solid base layer samples.

By "liquids" in the sense of the invention are to be understood all substances whose viscosity is so low that they can be distributed wettingly over the surface of a solid sample. They may also include substances in paste form.

I claim:

1. An assembled sample for determining materials of suitable colors for the base and top layer of a tooth repair component, comprising:
   a base layer color sample;
   a top layer color sample;
   wherein one of the base or top layer color samples is in the form of a liquid optically connected without bonding to the other layer.

2. The assembled sample according to claim 1, wherein the base layer color sample is an opaque liquid.

3. The assembled sample according to claim 2, wherein the liquid is colored.

4. The assembled sample according to claim 1, wherein the base layer color sample is solid, said assembled sample further including another solid layer color sample overlapping and optically connected with said top layer color sample.

5. A sample set for determining materials of suitable colors for the base and top layers of a tooth repair component with the aid of samples composed of a plurality of layers, comprising:
   at least one solid base layer color sample;
   at least one solid top layer color sample, each of said top layer color samples adapted for selective overlapping positioning of one of said base layer color samples; and
   a supply of liquid for application between the base and top layer color samples to optically connect the layers without bonding the layers.

6. A method of determining materials of suitable colors for the base and top layers of a tooth repair component comprising:
   (a) selecting a base layer color sample;
   (b) selecting a top layer color sample;
   (c) overlapping the top and base layer color samples;
   (d) introducing a liquid between the overlapping layer color samples to optically connect the samples and form an assembled component sample;
   (e) comparing the color of the component sample to the color of a natural tooth;
   (f) determining whether the color of the component sample satisfactorily matches the color of the natural tooth and if not,
   (g) repeating steps (a)–(f) until a satisfactory component sample is assembled.

7. The method according to claim 6, wherein the base and top layer color samples are solid and a colorless, transparent liquid is introduced between the base layer and top layer color samples, wetting them both.

8. The method according to claim 7, wherein the liquid is colored.

9. The sample set according to claim 5, wherein the liquid is transparent and colored.

10. The sample set according to claim 5, wherein the liquid is opaque.

* * * * *

UNITED STATES PATENT AND TRADEMARK OFFICE
CERTIFICATE OF CORRECTION

PATENT NO. : 4,715,813
DATED : December 29, 1987
INVENTOR(S) : Ernst Muhlbauer

It is certified that error appears in the above-identified patent and that said Letters Patent is hereby corrected as shown below:

Column 3, line 8 of claim 5, "of" (first occurrence) should be --on-- .

Signed and Sealed this

Tenth Day of November, 1992

*Attest:*

DOUGLAS B. COMER

*Attesting Officer*   *Acting Commissioner of Patents and Trademarks*